United States Patent
Gopin et al.

(10) Patent No.: US 9,617,241 B2
(45) Date of Patent: Apr. 11, 2017

(54) INTERMEDIATE COMPOUNDS AND PROCESS FOR THE PREPARATION OF EFINACONAZOLE

(71) Applicant: MAPI PHARMA LTD., Ness Ziona (IL)

(72) Inventors: Anna Gopin, Petach-Tikva (IL); Shai Rubnov, Tel Aviv (IL); Galina Zats, Ramat Gan (IL); Ehud Marom, Kfar Sava (IL)

(73) Assignee: MAPI PHARMA LTD., Ness Ziona (IL)

( * ) Notice: Subject to any disclaimer, the term of this patent is extended or adjusted under 35 U.S.C. 154(b) by 0 days.

(21) Appl. No.: 14/890,354

(22) PCT Filed: Mar. 2, 2015

(86) PCT No.: PCT/IL2015/050222
§ 371 (c)(1),
(2) Date: Nov. 10, 2015

(87) PCT Pub. No.: WO2016/079728
PCT Pub. Date: May 26, 2016

(65) Prior Publication Data
US 2016/0355500 A1 Dec. 8, 2016

Related U.S. Application Data

(60) Provisional application No. 62/083,233, filed on Nov. 23, 2014.

(51) Int. Cl.
*C07D 401/06* (2006.01)
*C07C 25/24* (2006.01)
*C07C 31/40* (2006.01)
*C07C 29/40* (2006.01)
*C07C 17/35* (2006.01)

(52) U.S. Cl.
CPC ............ *C07D 401/06* (2013.01); *C07C 17/35* (2013.01); *C07C 25/24* (2013.01); *C07C 29/40* (2013.01); *C07C 31/40* (2013.01)

(58) Field of Classification Search
CPC ....... C07D 401/06; C07C 17/35; C07C 25/24; C07C 29/40; C07C 31/40
USPC ...................................................... 546/210
See application file for complete search history.

(56) References Cited

U.S. PATENT DOCUMENTS

| 5,648,372 | A | 7/1997 | Naito |
| 5,716,969 | A | 2/1998 | Naito |
| 5,792,781 | A | 8/1998 | Naito |
| 5,962,476 | A * | 10/1999 | Naito ................... C07D 231/12 514/326 |
| 8,039,494 | B1 | 10/2011 | Winckle |
| 8,486,978 | B2 | 7/2013 | Winckle |
| 8,871,942 | B2 * | 10/2014 | Mimura ............... C07D 401/06 546/210 |
| 9,493,428 | B2 * | 11/2016 | Wilhelm .............. C07D 249/08 514/9 |
| 2013/0150586 | A1 | 6/2013 | Mimura |

FOREIGN PATENT DOCUMENTS

| EP | 1693358 A1 | 8/2006 |
| EP | 2128155 A1 | 12/2009 |
| EP | 2612859 A1 | 7/2013 |
| JP | 10212287 A | 8/1998 |
| WO | 94/26734 A1 | 11/1994 |
| WO | 2005/115398 A2 | 12/2005 |

OTHER PUBLICATIONS

Kishi et al. "Method for the preparation of triazole . . . " CA152:429720 (2010).*
Acetti et al., (2009) Enzyme-catalysed approach to the preparation of triazole antifungals: synthesis of (−) genaconazole. Tetrahedron: Asymmetry 20: 2413-2420.
Bennett et al., (1995) An Enantioselective Synthesis of the Antifungal Agent (2R, 3R)-2-(2,4-Difluorophenyl)-3-methylsulfonyl)-1-(1,2,4-triazol-1-yl)-2-butanol (Sch 42427; SM 9164). Synlett 1995(11): 1110-1112.
Kaku et al., (1998) A Novel Route for Chiral Synthesis of the Triazole Antifungal ER-30346. Chemical & Pharmaceutical Bulletin 46(7): 1125-1129.
Konosu et al., (1991) Concise synthesis of optically active oxirane precursors for the preparation of triazole antifungals using the Friedel-Crafts reaction of (S)-2-tosyloxypropionyl chloride. Tetrahedon Lett 32(51): 7545-7548.
Konosu et al., (1991) Triazole antifungals. III. Stereocontrolled synthesis of an optically active triazolylmethyloxirane precursor to antifungal oxazolidine derivatives. Chem Pharm Bull 39(9): 2241-6.
Miyauchi et al., (1996) Asymmetric Synthesis of SM-9164, a Biologically Active Enantiomer of Antifungal Agent SM-8668. Bulletin of the Chemical Society of Japan 69(9): 2625-2632.
Pesti et al., (2009) The Process Development of Ravuconazole: An Efficient Multikilogram Scale Preparation of an Antifungal Agent. Org Process Res Dev 13(4): 716-728.
Tamura et al., (2014) An Enantioselective Synthesis of the Key Intermediate for Triazole Antifungal Agents; Application to the Catalytic Asymmetric Synthesis of Efinaconazole (Jublia). J Org Chem 79(7): 3272-3278.
Tasaka et al., (1993) Optically active antifungal azoles. I. Synthesis and antifungal activity of (2R,3R)-2-(2,4-difluorophenyl)-3-mercapto-1-(1H-1,2,4-triazol-1-yl)-2-butanol and its stereoisomers. Chem Pharm Bull (Tokyo) 41(6): 1035-42.

(Continued)

*Primary Examiner* — Celia Chang
(74) *Attorney, Agent, or Firm* — Rothwell, Figg, Ernst & Manbeck, P.C.

(57) ABSTRACT

The present invention relates to a process for the preparation of (2R,3R)-2-(2,4-difluorophenyl)-3-(4-methylene-1-piperidinyl)-1-(1H-1,2,4-triazol-1-yl)-2-butanol (Efinaconazole) and intermediates used in such process.

19 Claims, No Drawings

(56) References Cited

OTHER PUBLICATIONS

Tsuruoka et al., (1998) Synthesis and antifungal activity of novel thiazole-containing triazole antifungals. II. Optically active ER-30346 and its derivatives. Chem Pharm Bull 46(4): 623-30.

* cited by examiner

INTERMEDIATE COMPOUNDS AND PROCESS FOR THE PREPARATION OF EFINACONAZOLE

CROSS REFERENCE TO RELATED APPLICATIONS

This application is a 35 U.S.C. §371 National Phase Entry Application from PCT/IL2015/050222, filed on Mar. 2, 2015, and designating the United States, which claims the benefit of U.S. Provisional Application No. 62/083,233 filed on Nov. 24, 2014, the entire disclosures of which are incorporated herein by reference in their entireties.

FIELD OF THE INVENTION

The present invention relates to a process for the preparation of (2R,3R)-2-(2,4-difluorophenyl)-3-(4-methylene-1-piperidinyl)-1-(1H-1,2,4-triazol-1-yl)-2-butanol (Efinaconazole) and intermediates in such process.

BACKGROUND OF THE INVENTION

Efinaconazole, chemically designated (2R,3R)-2-(2,4-Difluorophenyl)-3-(4-methylene-1-piperidinyl)-1-(1H-1,2,4-triazol-1-yl)-2-butanol, also known as Jublia or KP-103, is the first triazol compound approved for a topical medication for onychomycosis.

Several patents and patent Publications (U.S. Pat. No. 5,716,969, WO 94/26734, US 2013/150586, WO 2005/115398, JP 10212287 and EP1693358); and scientific publications (Konosu, T. et al. *Chem. Pharm. Bull*, 1991, 39(9), 2241; Tasaka, A. et al. *Chem. Pharm. Bull.*, 1993, 41 (6), 1035; Konosu, T. et al. *Tetrahedron Lett.*, 1991, 32(51), 7545; Bennett, F. et al. *SYNLETT*, 1995, 1110; Acetti, D. et al. *Tetrahedron: Asymmetry* 2009, 20, 2413; and Pesti, J. et al. *Org. Process Res. Dev.* 2009, 13, 716) disclose processes for the preparation of Efinaconazole by interaction of (2R,3S)-2-(2,4-difluorophenyl)-3-methyl-2-[(1H-1,2,4-triazol-1-yl)methyl]-oxirane ("epoxytriazole") with 4-methylenepiperidine. Also disclosed are Efinaconazole intermediates and building blocks.

Since Efinaconazole contains two adjacent chiral centers, the synthesis of enantiomerically pure compound is complex and thus far, all the known syntheses are not efficient enough and do not enable a cost effective manufacturing procedure on a commercial scale.

U.S. Pat. No. 5,648,372 and U.S. Pat. No. 5,792,781 describe enantioselective synthesis of compounds related to Efinaconazole from chiral 3-hydroxy-2-methyl propionic acid in 12 steps with an overall yield lower than 5%. In another approach comprised of 13 steps and low overall yield, (R)-lactic acid was used as the starting material (Tsuruoka, A. et al. *Chem. Pharm. Bull.* 1998, 46(4), 623 and Kaku, Y. et al., ibid. 1998, 46(7), 1125). Because both starting materials contain only one chiral center, the second, adjacent chiral center has to be created by a diastereoselective reaction (using either Corey or Sharpless epoxidation method). However, this reaction is not sufficiently selective leading mostly to a mixture of two diastereomers which have to be separated. The second approach, for synthesis of ("epoxytriazole") based on (R)-methyl lactate, was optimized on a multi kilogram scale (Pesti, J. et al. *Org. Process Res. Dev.*, 2009, 13, 716), but still involves 8 manufacturing steps (scheme 1), with an overall yield of 16%, which is not cost effective for commercial scale production:

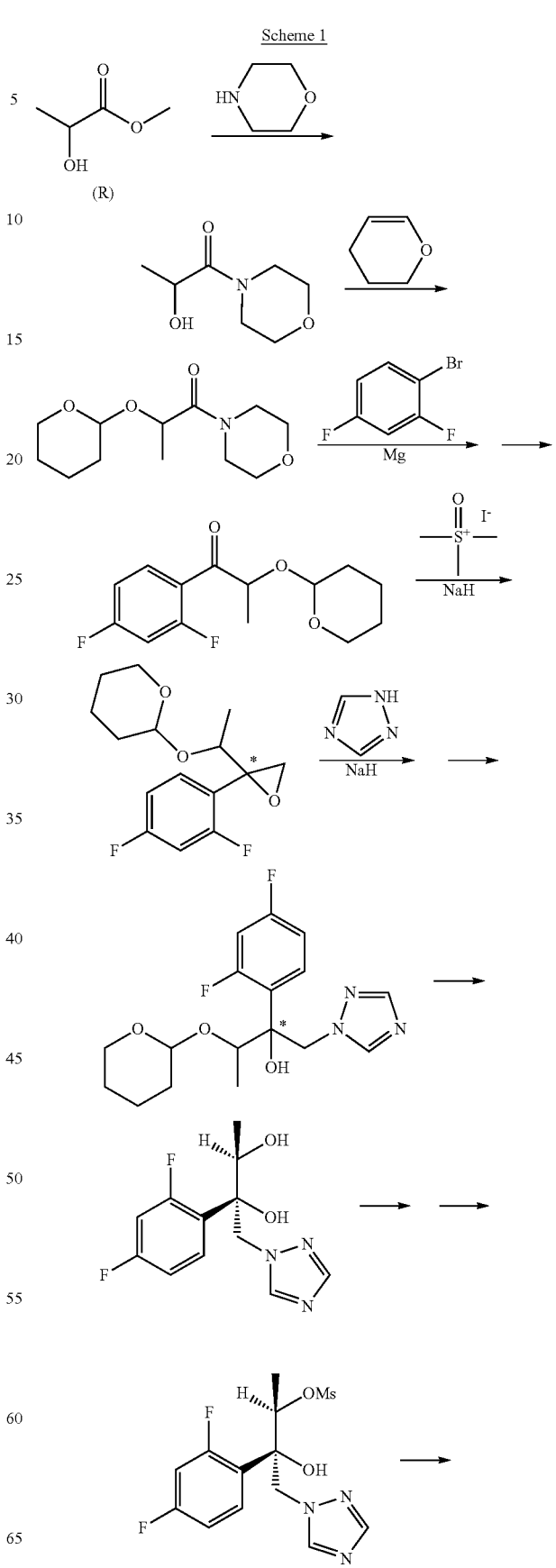

Scheme 1

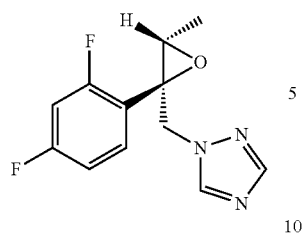

Another approach, using catalytic asymmetric cyanosilylation of 2-chloro-1-(2,4-difluorophenyl) ethanone (2') was described (Tamura, K. et al., *J. Org. Chem.*, 2014, 79, 3272), claiming the shortest method reported to date for Efinaconazole synthesis. The method comprises 7 steps, in which four steps have performed as two "one-pot" synthesis:

Scheme 2

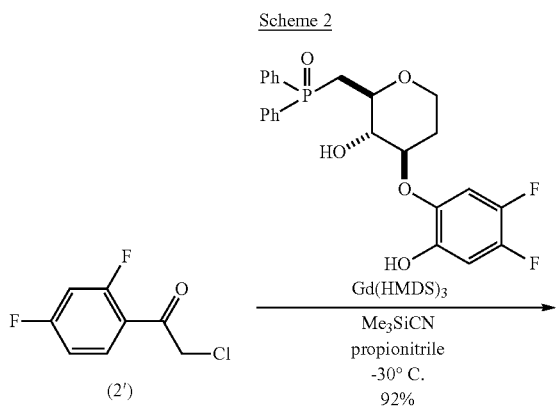

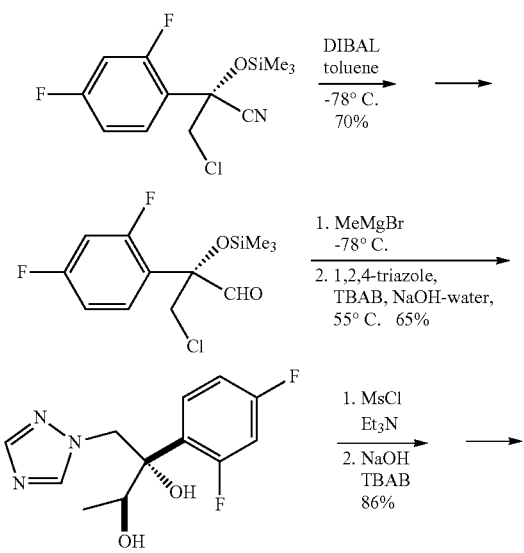

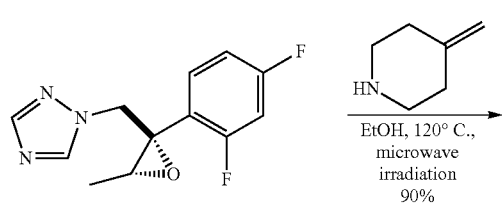

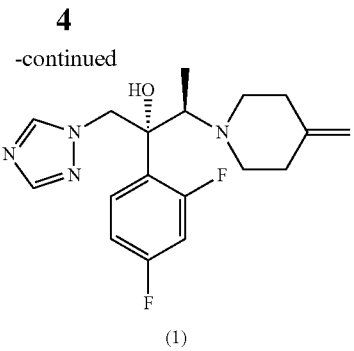

(1)

However, the procedure has several potential drawbacks as a method for large-scale synthesis. Aside from the use of the non-commercially-available sugar-derived chiral ligand, the use of gadolinium bis(trimethylsilyl)amide is problematic: it is corrosive, reacts vigorously with water, and should be manipulated with air-free technique in extra dry solvents. In addition, the process is conducted in cryogenic conditions (T=−78° C.), which requires special equipment and employs microwave irradiation, a technique typically used in laboratory scale, with limited industrial applicability.

Another disadvantage of the aforementioned process is the use of hazardous materials such as diisobutylaluminium hydride (DIBAL), a combustible reagent which reacts violently with air and water. In addition, the use of DIBAL leads to poor atom economy of the reaction, yielding voluminous aluminum salts, which have to be separated from the product and disposed of. The cost of such hazardous material disposal is considerable.

Therefore, there continues to be a need in the art for a practical method for making Efinaconazole, which not only avoids the problems of the existing art, but is also safe, cost effective, and industrially feasible.

SUMMARY OF THE INVENTION

The present invention provides a process for preparing Efinaconazole which comprises an improved method for preparing the Efinaconazole intermediate (6), and its reaction with 4-methylenepiperidine to produce Efinaconazole. The process of the invention overcomes the problems associated with the prior art processes and is amenable to scale-up for industrial production.

The process of the invention comprises the following steps:

a) reacting ketone (2) with an organometallic alkylating agent capable of introducing an ethyl group, to form an alcohol of formula (3);

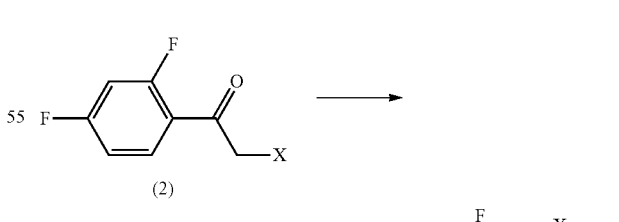

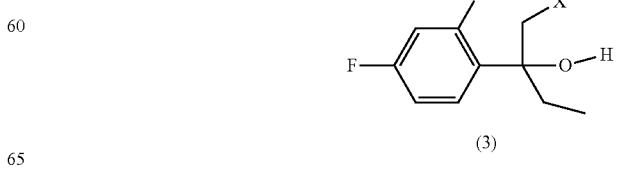

wherein X is a leaving group;

b) converting alcohol (3) to an alkene of formula (4);

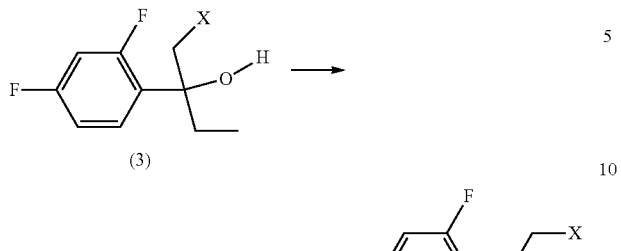

c) reacting alkene (4) with 1,2,4-triazole to form 1-(2-(2,4-difluorophenyl)but-2-en-1-yl)-1H-1,2,4-triazole (5);

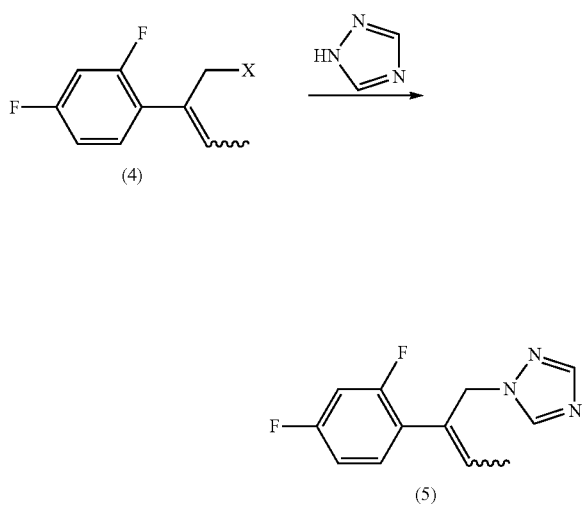

d) epoxidation of triazole-containing alkene (5), to form 1-((2-(2,4-difluorophenyl)-3-methyloxiran-2-yl)methyl)-1H-1,2,4-triazole (6); and

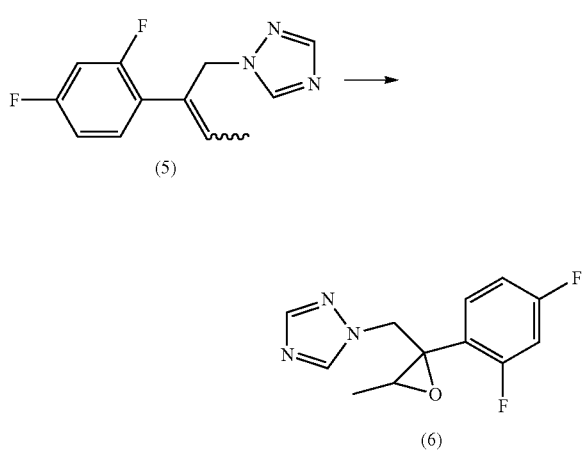

e) formation of Efinaconazole (1) by reacting epoxide (6) with 4-methylenepiperidine

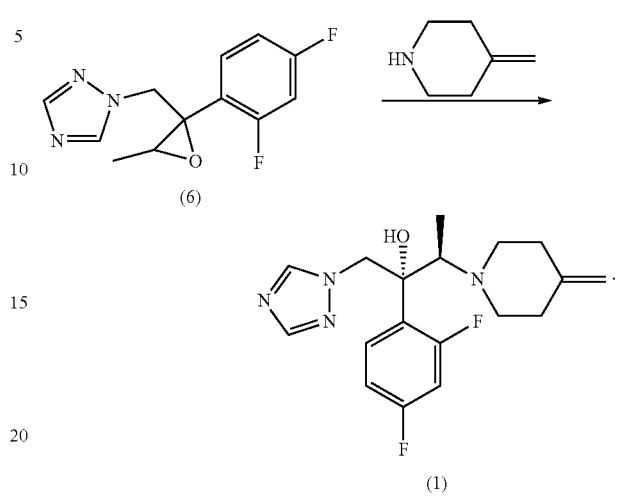

In some embodiments, the leaving group is selected from the group consisting of halogen, sulfonyloxy and —OC(O)R' wherein R' is an alkyl, aryl or alkylaryl. In some preferred embodiments, the leaving group is selected from the group consisting of Cl, Br, I, mesylate (OMs), triflate (OTr) and tosylate (OTs). In a currently preferred embodiment, the leaving group X is Cl. Each possibility represents a separate embodiment of the present invention.

In some embodiments, the organometallic alkylating agent is selected from ethyl lithium (EtLi) and ethyl magnesium halogenate (Et-Mg—Y wherein Y is halogen). In some currently preferred embodiments, the organometallic alkylating agent is ethyl magnesium chloride or ethyl magnesium bromide. Each possibility represents a separate embodiment of the invention.

In some embodiments, step (b) is conducted in the presence of a dehydration agent, preferably a strong protic acid such as sulfuric acid or phosphoric acid.

In some embodiments, step (c) is conducted in the presence of a base which may be selected from metal hydride compounds (e.g., sodium hydride, potassium hydride, etc.) alcoholates (e.g., NaOMe, NaOEt, t-BuONa, t-BuOK etc.), hydroxides, carbonates, bicarbonates, organic amines and basic resins. Preferred bases are metal hydrides or alcoholates. Each possibility represents a separate embodiment of the present invention. The reaction may be conducted in a polar aprotic solvent, such as dimetylformamide (DMF), dimethylsulfoxide (DMSO), N-methylpyrrolidone (NMP). Each possibility represents a separate embodiment of the present invention.

In some embodiments, steps (a), (b) and (c) of the process are conducted as "one-pot" synthesis without separation and purification of corresponding intermediates.

In other embodiments, step (d) is carried out in the presence of an epoxidation agent, preferably, a peroxy organic acid such as peroxymaleic acid.

The present invention also relates to certain intermediates formed in the aforementioned process. In one embodiment, the present invention relates to a compound represented by the formula (3), for example a compound represented by the structure of formula (3'). In another embodiment, the present invention relates to a compound represented by the formula (4), for example a compound represented by the structure of formula (4'), including its (Z)- or (E)-isomers or mixture thereof. Each possibility represents a separate embodiment of the present invention. The structures of compounds (3), (3'), (4) and (4') are provided in the detailed description hereinbelow.

DETAILED DESCRIPTION OF THE INVENTION

The present invention relates to a process for the preparation of (2R,3R)-2-(2,4-difluorophenyl)-3-(4-methylene-1-piperidinyl)-1-(1H-1,2,4-triazol-1-yl)-2-butanol (Efinaconazole). The present invention further relates to certain intermediates formed in such processes.

CHEMICAL DEFINITIONS

An "alkyl" group refers to any saturated aliphatic hydrocarbon, including straight-chain, and branched-chain groups. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. Each possibility represents a separate embodiment of the present invention. The term haloalkyl refers to an alkyl group as defined herein which is substituted by one or more halogen atoms.

An "aryl" group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. Each possibility represents a separate embodiment of the present invention.

An "alkylaryl" group is an alkyl group as defined herein bonded to an aryl group as defined herein. The aryl group can be unsubstituted or substituted through available carbon atoms with one or more groups defined hereinabove for alkyl. The alkylaryl group may be attached to the rest of the molecule through the alkyl or aryl moiety.

The present invention provides a process for preparing Efinaconazole illustrated in Scheme 3.

Scheme 3

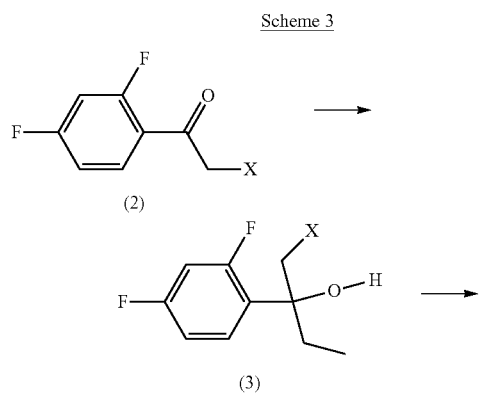

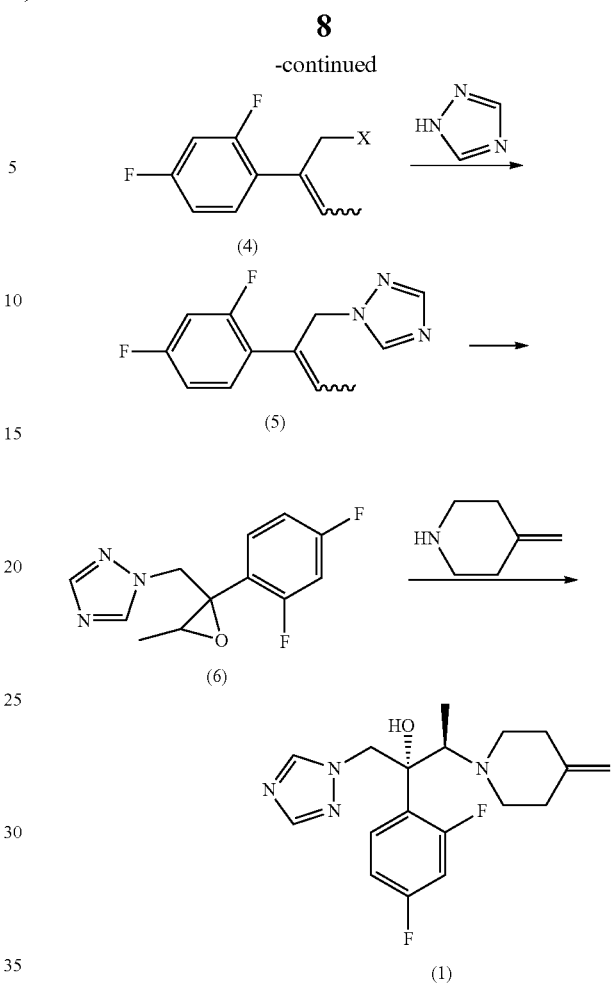

wherein X is a leaving group.

Any leaving group can be used in step (a) of the process of the invention. In some embodiments, the leaving group is selected from the group consisting of halogen, sulfonyloxy and —OC(O)R' wherein R' is an alkyl, aryl or alkylaryl. In some preferred embodiments, the leaving group is selected from the group consisting of Cl, Br, I, mesylate (OMs), triflate (OTr) and tosylate (OTs). In a currently preferred embodiment, the leaving group X is Cl. Each possibility represents a separate embodiment of the present invention.

Any organometallic alkylating agent that is capable of introducing an ethyl group can be used in step (a) of the process of the invention. In some embodiments, the organometallic alkylating agent is selected from ethyl lithium (EtLi) and ethyl magnesium halogenate (Et-Mg—Y wherein Y is halogen). Additional organometallic reagents include, but are not limited to, $Et_3Al$, $Et_2Zn$, $Et_2CuLi$, $Et_2CuMgX$ wherein X is halogen, $Et_2Cu(CN)Li_2$, and the like. In some currently preferred embodiments, the organometallic alkylating agent is ethyl magnesium chloride or ethyl magnesium bromide. Each possibility represents a separate embodiment of the present invention.

In a particular embodiment of the process of the invention, X is Scheme 3 is a halogen, preferably Cl, and step (a) involves the use of ethyl magnesium halogenate (EgMgY). In accordance with this preferred embodiment, the process is illustrated in Scheme 4 hereinbelow.

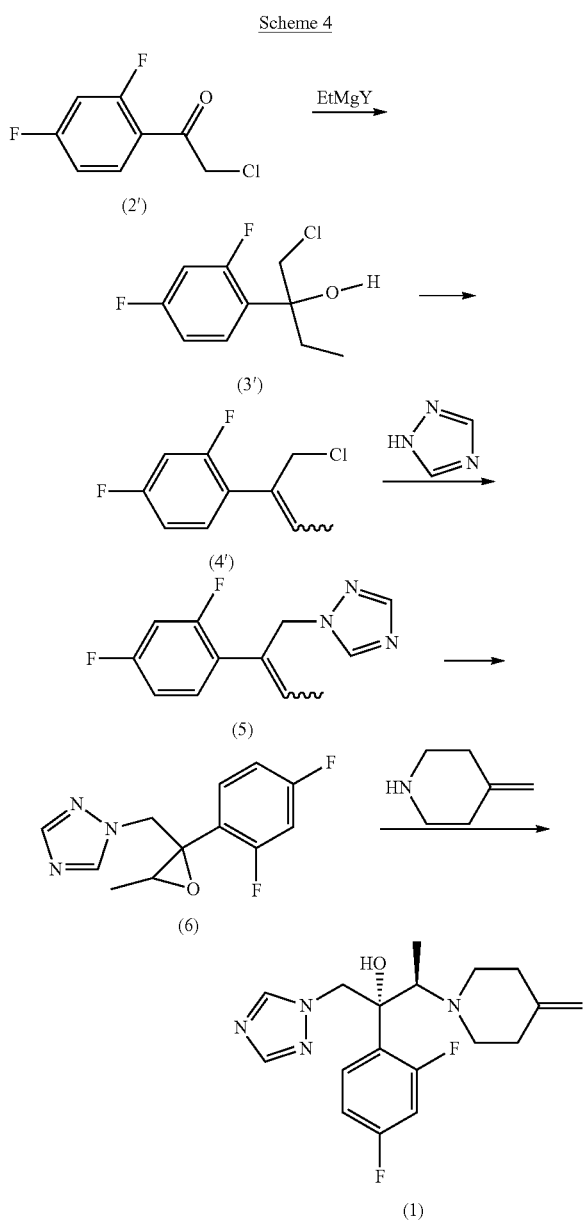

Further reference to alternative embodiments of the process of the invention will now be made. It is apparent to a person of skill in the art, however, that any description provided herein is representative in nature and should not be construed as limiting the broad scope of the present invention.

Step (a) of the process of the invention comprises reacting ketone (2) (Scheme 3) or (2') (Scheme 4) with a solution of an organometallic alkylating agent capable of introducing an ethyl group, preferably ethyl magnesium halogenate EtMgY, wherein Y=Cl, Br or I or ethyl lithium. The process may be conducted in organic solvents, such as toluene and/or ethers (e.g., MTBE, THF, 2-Me-THF), preferably, toluene. This step leads to the formation of alcohol (3), for example 1-chloro-2-(2,4-difluorophenyl)butan-2-ol (3'). Ethyl magnesium halogenate is a currently preferred organometallic alkylating agent for this step. A solution of ethyl magnesium halogenate is commercially available, for example, for EtMgBr as 25% solution in THF (typ. 2.8 M), 15% solution in MTBE (typ. 0.9 M) 40% solution in 2-Me-THF (typ. 3.4 M), or for EtMgCl as 25% solution in THF (typ. 2.8 M) from Rockwood Lithium Co.

In compound (2), the group X may be any leaving group known to a person of skill in the art, for example a halogen (F, Cl, Br or I), or a sulfonyloxy (e.g., mesylate (OMs), triflate (OTr), tosylate (OTs) and the like). Other examples of X include —OC(O)R' wherein R' is an alkyl, aryl or alkylaryl. Preferably, the leaving group X is a halogen, and most preferably chlorine as exemplified in compounds (2'), (3') and (4'). Each possibility represents a separate embodiment of the present invention.

The reaction is preferably carried out at a temperature range of about -20° C. to about 50° C., especially from about 0° C. to about 30° C., more preferably from about 5° C. to about 15° C. The reaction time is generally from about 15 minutes to about 48 hours, preferably from about 0.5 to about 2 hours.

In the next step of the process, step (b), alcohol (3) (Scheme 3) or (3') (Scheme 4) is dehydrated by using a dehydrating reagent to form the corresponding alkene (4) or (4'). Suitable dehydrating reagents can be selected from the compounds described in the chapter "Dehydration of alcohols" in Comprehensive Organic Transformations: A Guide to Functional Group Preparations, Richard C. Larock, Wiley, 1999, p. 291-293, the contents of which are hereby incorporated by reference in their entirety. One example of suitable dehydrations are Brønsted acids, and more preferably strong protic acids, such as sulfuric acid or phosphoric acid. The reaction can be carried out in neat conditions (no solvent) or with the aid of a solvent. Current preference is given to toluene and the reaction is carried out with heating (from about 40° C. to reflux).

Step (c) of the process comprises reacting chloro-containing alkene (4) (Scheme 3) or (4') (Scheme 4) with 1,2,4-triazole in the presence of a base with formation of the corresponding derivative 1-(2-(2,4-difluorophenyl)but-2-en-1-yl)-1H-1,2,4-triazole (5).

Examples of suitable bases include, but are not limited to: 1) metal hydride compounds (e.g., alkali metal hydrides such as sodium hydride (NaH), potassium hydride (KH), etc.), organometallic compounds (e.g., compounds having direct chemical bond between an alkali metal and $C_{1-4}$ alkyl group such as organolithium compounds, e.g., methyllithium, n-butyllithium, etc.); 2) metal alcoholates (e.g., compounds in which a hydroxy hydrogen of $C_{1-4}$ alcohols is replaced by an alkali metal such as sodium methoxide (NaOMe), sodium ethoxide (NaOEt), sodium t-butoxide (t-BuONa), potassium methoxide (KOMe), potassium ethoxide (KOEt), potassium t-butoxide (t-BuOK), lithium methoxide (LiOMe), lithium ethoxide (LiOEt), lithium t-butoxide (t-BuOLi), etc.); 3) alkali metal hydroxides (e.g., NaOH, KOH, etc.); 4) carbonates (e.g., alkali metal salts of carbonate such as sodium carbonate, potassium carbonate, etc., or alkaline-earth metal salts of carbonate such as calcium carbonate, magnesium carbonate, etc.); 5) bicarbonates (e.g., alkali metal salts of bicarbonate such as sodium bicarbonate, potassium bicarbonate, etc.); 6) organic amine bases (e.g., trimethylamine, triethylamine, diisopropylethylamine, pyridine, picoline, N-methylpyrrolidine, N-methylmorpholine, 1,5-diazabicyclo[4.3.0]non-5-ene, 1,4-diazabicyclo[2.2.2]octane, 1,8-diazabicyclo [5.4.0]-7-undecene, etc.); and 7) basic resin and polymers such as Amberlyst A-26 resin (OH-form). Currently preferred bases are metal hydride compounds (e.g., sodium hydride, potassium hydride, etc.) or alcoholates (e.g., NaOMe, NaOEt, t-BuONa, t-BuOK, etc.). Each possibility represents a separate embodiment of the present invention.

Suitable organic solvents for use in this step include, but are not limited to aromatic hydrocarbons, esters, ethers, nitriles, ketones, amides, sulfoxides and mixtures thereof; preferably polar solvents, more preferably, DMF, DMSO, or NMP. Each possibility represents a separate embodiment of the present invention.

The reaction is carried out with heating (from about 50° C. to reflux, preferably, at about 120-140° C.).

The reaction steps (a)-(c) can be performed sequentially, or as "one-pot" synthesis without separation and purification of intermediates (3) and (4), which significantly simplifies preparation and improve economical parameters of the process.

In the next step (d), epoxide (6) formation is carried out by epoxidation of triazole-containing alkene (5). Any epoxidation reagent can be used in this step, for example any of the reagents, described in Comprehensive Organic Synthesis: Oxidation by Editor-in-Chief: Barry M. Trost and Ian Fleming, Elsevier, 1991—Science, v. 7, pp. 357-436, the contents of which are hereby incorporated by reference in their entirety. Currently preferred epoxidation agents are peroxy acids, for example peroxymaleic acid. This acid is slightly less reactive than peroxytrifluoroacetic acid, but more reactive than most other usual peroxy acids and it has the advantage that, as oxidation proceeds, the reduction product, maleic acid, precipitates out of the solution. It may easily be removed by filtration, when oxidation is complete and recycled. Other peroxy acids that may be used for this step include, but are not limited to, any molecule of the formula R—C(=O)—OOH wherein R is alkyl, haloalkyl, aryl or alkylaryl, for example meta-Chloroperbenzoic acid, Peracetic Acid, Trifluoroacetic peracid, and the like.

The final step (e), formation of Efinaconazole, may performed by any method known to a person of skill in the art, for example as described in U.S. Pat. No. 5,716,969; WO 94/26734; US 2013/150586; or EP 2128155, the contents of each of which is hereby incorporated by reference in its entirety.

Intermediates

Certain intermediates produced by the process described herein are novel and represent further embodiments of the present invention. For example, in one embodiment, the present invention provides an intermediate compound represented by the structure of formula (3):

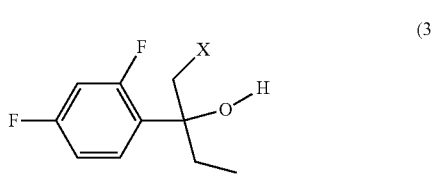

wherein X is a leaving group selected from the group consisting of Cl, Br, I, mesylate (OMs), triflate (OTr) and tosylate (OTs).

In one embodiment of compound (3), X is Cl and the compound is represented by the structure of formula (3'):

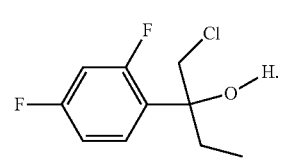

In another embodiment, the present invention provides an intermediate compound represented by the structure of formula (4):

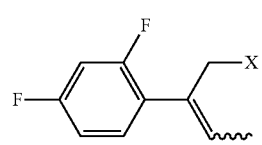

including (Z)- or (E)-isomers or mixtures thereof, wherein X is a leaving group selected from the group consisting of Cl, Br, I, mesylate (OMs), triflate (OTr) and tosylate (OTs).

In one embodiment of compound (4), X is Cl and the compound is represented by the structure of formula (4'):

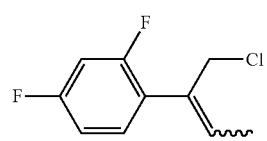

including (Z)- or (E)-isomers or mixtures thereof.

The following examples are given for the purpose of illustrating the present disclosure and should not be considered as limitation on the scope or spirit of the invention.

EXPERIMENTAL SECTION

Certain compounds which are representative of this invention were prepared as per the following examples and reaction sequences. No attempt has been made to optimize the yields obtained in any of the reactions. Unless otherwise noted, the materials used in the examples were obtained from readily available commercial suppliers or synthesized by standard methods known to one skilled in the art of chemical synthesis. The work-up treatment in each step can be applied by a typical method, wherein isolation and purification is performed as necessary by selecting or combining conventional methods, such as crystallization, recrystallization, distillation, partitioning, column chromatography, preparative HPLC and the like.

Example 1

Preparation of 1-chloro-2-(2,4-difluorophenyl)butan-2-ol (3')

A solution of 2-chloro-2',4'-difluoro-acetophenone (2') (10 g, 52.5 mmol) in dry toluene (25 ml) was added dropwise over 1 h to a stirred solution of commercially available EtMgBr (3M solution in diethyl ether) (21 ml, 62.9 mmol) cooled to 5° C. The reaction temperature was kept at 10-15° C. After completion of addition, the reaction mixture was stirred at 15° C. for 30 min and monitored by GC or HPLC.

After completion of the reaction, the reaction mixture was poured in small portions into a cooled solution of 1M HCl (50 ml) while stirring and verifying that the pH of the mixture was about 5. The stirring was stopped and the organic phase was separated and kept aside. The aqueous phase was washed twice with 50 ml toluene and the combined organic phases were washed once with brine (50 ml), dried over $Na_2SO_4$ and concentrated under reduced pressure. Yield: 11.6 g.

The crude product was used in the next step without additional purification $^1$H NMR (CDCl$_3$, 400 MHz) δ: 7.63-7.56 (1H, m); 6.93-6.88 (1H, m); 6.81-6.78 (1H, m); 4.09 (1H, d, J=10.8 Hz); 3.88 (1H, dd, J=12, J=1.2 Hz); 2.05-1.97 (1H, m); 1.94-1.87 (1H, m); 0.78 (3H, t, J=8 Hz)

GC conditions: Column: DB-1301, Ser. #USC705322, Length: 30 m, D=0.32, film thickness 1uM; Flow rate: He: 30 ml/min, H2: 40 ml/min, Air: 400 ml/min. Diluent: MeOH; Column conditions: T[min]/temp[° C.] (hold[min]): 0/120 (2); 15/240(5). Retention time: 10.5 min HPLC conditions: Column: Hypersil Gold (Thermo) C18 (150×4.63μ); Mobile phase: A: H$_2$O (0.1% TFA), B: Acetonitrile (0.1% TFA); T/% B: 0/5; 0.5/5; 10/100; 11/100; 12/5; 16/5. Flow rate: 1.3 ml/min. Diluent: MeOH. Retention time: 6.8 min.

Example 2

Preparation of 1-(1-chlorobut-2-en-2-yl)-2,4-difluorobenzene (4')

To a stirred solution of Compound 3' (6.6 g, 29.9 mmol) in toluene (30 ml), H$_2$SO$_4$ (50%) was added (5.34 g, 4.11 ml, 29.9 mmol). After addition, the reaction mixture was heated to reflux and water was distilled by Dean-Stark apparatus. The reaction was monitored by GC. After completion of the reaction, the reaction mixture was cooled to RT. Toluene (50 ml) was added. The mixture was washed with three portions of water (50 ml), then once with brine, dried over Na$_2$SO$_4$ and then the solvent was evaporated. Yield: 5.83 g.

The crude product was used in the next step without additional purification.

$^1$H NMR (CDCl$_3$, 400 MHz) δ: 7.28-7.16 (1H, m); 6.87-6.77 (2H, m); 5.90-5.85 (1H, dd, J=7.2, J=6.8 Hz); 4.44 (2H, s); 1.90 (3H, d, J=6.8 Hz).

GC conditions: the same as in example 1. Retention time: 9.97 min

HPLC Conditions: the same as in example 1. Retention time: 7.9 min

Example 3

Preparation of 1-(2-(2,4-difluorophenyl)but-2-en-1-yl)-1H-1,2,4-triazole (5)

a). 1,2,4-Triazole (3.43 g, 49.7 mmol) was added portionwise to a suspension of sodium hydride (60% in mineral oil) (1.99 g, 49.7 mmol) in dry DMF (10 ml) at RT and the mixture was stirred until effervescence ceased. Compound 4' (6.7 g, 33 mmol) was added dropwise and the solution heated to 140° C. for one hour. The reaction progress was monitored by GC. After reaction completion, the reaction mixture was cooled to RT. The reaction mixture was poured in water (50 ml), acidified with 1N HCl solution to pH 1, extracted with Hexane (3×50 ml); later the acidic solution was extracted with EtOAc (3×50 ml); then each combined organic layer was washed once with brine solution. The combined organic layer was dried over Sodium sulfate and concentrated under reduced pressure. The crude product was purified by column chromatography using 230-400 mesh silica gel starting from Hexane:EtOAc=9:1 and using Hexane:EtOAc gradient to obtain the desired product as yellow solid.

Yield: 62% as a mixture of two isomers (81% of desired isomer).

Isomer I (desired compound):
$^1$H NMR (CDCl$_3$, 400 MHz) δ: 8.03 (1H, s); 7.88 (1H, s); 7.06-7.03 (1H, m); 6.79-6.74 (2H, m); 6.01 (1H, q, J=6.8 Hz); 5.20 (2H, s); 1.9 (3H, d, J=6.8 Hz)

Isomer II
$^1$H NMR (CDCl$_3$, 400 MHz) δ: 8.10 (1H, s); 7.92 (1H, s); 6.93-6.87 (1H, m); 6.85-6.76 (2H, m); 6.08-6.03 (1H, m); 5.02 (2H, s); 1.61 (3H, dd, J=6.4 Hz, J=0.4 Hz)

GC conditions: Retention time 15.67 min (for isomer I); 14.9 min (for isomer II)

HPLC conditions: Retention time 5.8 min (for isomer I).

b). A suspension of sodium hydride (60% in mineral oil) (1.99 g, 49.7 mmol) was added to dry DMSO (8 ml) under nitrogen. The mixture was heated for a period of 45 min after sodium hydride addition with vigorous stirring under a slow stream of nitrogen. Completion of the reaction was shown by the disappearance of sodium hydride and the cessation of hydrogen evolution. The final solution was grey-brown. 1,2,4-Triazole (3.43 g, 49.7 mmol) was added portionwise to sodium methylsulfinylmethylide (Na-dimsyl) solution at RT and the solution stirred until gas evolution ceased. Compound (4') (6.7 g, 33 mmol) in 10 ml of dry DMSO was added dropwise and the solution was stirred at 140-145° for one hour. The reaction progress was monitored by GC. After completion of the reaction, the reaction mixture was cooled to RT, and poured into water (50 ml), acidified with 1N HCl solution to pH 1, extracted with EtOAc (3×50 ml); and the combined organic layer was washed once with brine solution. The organic layer was dried over Sodium sulfate and concentrated under reduced pressure. The crude product was purified by column chromatography using 230-400 mesh silica gel starting from Hexane:EtOAc=9:1 and using Hexane:EtOAc gradient to obtain the desired product as yellow solid.

Yield: 83% as a mixture of two isomers (89% of desired isomer).

Example 4

Preparation of 1-(2-(2,4-difluorophenyl)but-2-en-1-yl)-1H-1,2,4-triazole (5) as a "one-pot" synthesis A solution of 2-chloro-2',4'-difluoro-acetophenone (2') (10 g, 52.5 mmol) in dry toluene (35 ml) was added dropwise over about 1 h to a stirred solution of commercially available EtMgBr (2.8 M solution in THF) (21 ml, 62.9 mmol) cooled to 5° C. The temperature was kept at 10-15° C. by cooling. After addition, the reaction mixture was stirred at 15° C. for 30 min and monitored by GC or HPLC. After completion of the reaction, the reaction mixture was poured in small portions into cooled HCl 1M (50 ml) with stirring. The pH of the mixture was verified to be acidic (about 5). The organic phase was separated and kept aside. The aqueous phase was extracted twice with EtOAc (50 ml). The organic extracts were combined with the toluene mixture and washed once with brine (50 ml). Ethyl acetate and THF were distilled off and to the remained toluene solution (~30 ml) H$_2$SO$_4$ (50%) was added (10 g, 8.0 ml, 60 mmol). After completion of addition, the reaction mixture was heated to reflux and water was distilled by Dean-Stark apparatus. The reaction was monitored by GC. After completion of the reaction, the reaction mixture was cooled to RT. Toluene (50 ml) was added. The mixture was washed with three portions of water (50 ml), then once with brine. To this solution 30 ml of DMSO was added and the toluene was distilled off using Dean-Stark receiver.

The residual solution was added to the solution of sodium salt of 1,2,4-triazole, prepared as described in example 3 (b) from a suspension of sodium hydride (60% in mineral oil) (3.8 g, 0.1 mol), 16 ml of dry DMSO and 1,2,4-triazole (6.8 g, 0.1 mol). The mixture was stirred at 140-145° C. for one hour. The reaction progress was monitored by GC. After completion of the reaction, the reaction mixture was cooled to RT. The reaction mixture was poured in water (50 ml), acidified with 1N HCl solution to pH 1, extracted with EtOAc (3×50 ml); and the combined organic layer was washed once with brine solution. The organic layer was dried over sodium sulfate and concentrated under reduced pressure. The crude product was purified by column chromatography using 230-400 mesh silica gel starting from Hexane:EtOAc=9:1 and using Hexane:EtOAc gradient to obtain the desired product as yellowish solid.

Yield: 85% as a mixture of two isomers (91% of desired isomer, according to GC and HPLC).

Example 5

Preparation of 1-((2-(2,4-difluorophenyl)-3-methyl-oxiran-2-yl)methyl)-1H-1,2,4-triazole (6)

Maleic anhydride (5.1 g, 52 mmol) was dissolved in dichloroethane (30 ml), and a catalytic amount (2 drops) of concentrated sulfuric acid was added followed by hydrogen peroxide (50% solution) (1.3 ml, 22.7 mmol). The reaction mixture was heated to 50° C., then a solution of compound 5 (1.53 g, 6.5 mmol) in 1,2-Dicholoroethane (20 ml) was added dropwise. The mixture was heated to 70° C. for 1 hr and monitored by GC.

After completion of the reaction, the reaction mixture was cooled to RT. The precipitated maleic acid was filtered off with suction and washed with dichloromethane (DCM) (3×30 ml). The organic phase was washed three times with 10% Na$_2$S$_2$O$_3$ solution, then once with sodium bicarbonate saturated solution, dried over sodium sulfate and concentrated under reduced pressure. The crude product was purified by column chromatography, yielding 1.05 g (62%) of desired product. GC retention time: 16.29 min.

$^1$H NMR (CDCl$_3$, 400 MHz) δ: 8.01 (1H, s); 7.83 (1H, s); 7.04-6.99 (1H, dq, J=8.4, J=6.4 Hz); 6.81-6.70 (2H, m); 4.89 (1H, d, J=14.8 Hz); 4.43 (1H, d, J=14.8 Hz); 3.19 (1H, q, J=5.6 Hz); 1.64 (3H, d, J=5.6 Hz)

Mass (TOF ES$^+$): m/z=252

Another isomer has GC retention time 15.81 min and $^1$H NMR (CDCl$_3$, 400 MHz) δ: 8.16 (1H, s); 7.89 (1H, s); 7.16-7.10 (1H, dq, J=8.4, J=6.0 Hz); 6.88-6.81 (2H, m); 4.82 (1H, d, J=14.8 Hz); 4.43 (1H, d, J=14.8 Hz); 3.18 (1H, q, J=5.6 Hz); 1.06 (3H, d, J=5.6 Hz)

Example 6

Preparation of 2-(2,4-Difluorophenyl)-3-(4-methylene-1-piperidinyl)-1-(1H-1,2,4-triazol-1-yl)-2-butanol To commercially available 4-methylenepiperidine hydrochloride (1.4 g, 10.5 mmol) was added a solution of 50% potassium hydroxide (11.2 ml). The mixture was stirred till complete dissolution and the resulting solution was extracted with ethyl ether (20 ml). The aqueous phase was extracted with additional two portions of ethyl ether (20 ml×2), the organic phases were combined and the diethyl ether was removed under vacuum. The residue was dissolved in acetonitrile (5 ml), and the epoxide (6) (100 mg, 0.39 mmol) was added followed by Lithium perchlorate (287 mg, 2.7 mmol). The mixture was refluxed for 24 hours in an oil bath at 100° C. The reaction progress was monitored by HPLC. After completion of the reaction, the reaction mixture was cooled to RT, and the acetonitrile was evaporated. Water (50 ml) was added to the residue. The product was extracted with three portion of EtOAc (30 ml). The combined organic layer was concentrated under reduced pressure. The crude product was purified by column chromatography using 230-400 mesh silica gel starting from Hexane:EtOAc=8:2 and using Hexane:EtOAc gradient to obtain the desired product as yellowish solid. Yield: 112 mg (82%).

No attempt has been made to improve the chiral purity of the product and purification may be performed as necessary by selecting or combining conventional methods, such as selective crystallization, recrystallization, distillation, partitioning, column chromatography, preparative HPLC and the like.

$^1$H NMR (CDCl$_3$, 400 MHz) δ: 8.01 (1H, s); 7.78 (1H, s); 7.54-7.48 (1H, m); 6.81-6.71 (2H, m); 5.46 (1H, bs); 4.90-4.86 (1H, dd, J=14.4, J=1.2 Hz); 4.82-4.78 (1H, dd, J=14.4, J=0.8 Hz); 4.64 (2H,$); 2.94-2.89 (1H, m); 2.72-2.67 (2H, m); 2.35 (2H, bs); 2.27-2.16 (4H, m); 0.96-0.94 (3H, dd, J=7.2, J=2.8 Hz). Mass (TOF ES$^+$): m/z=349 [M+H]$^+$ The contents of each of the references cited herein is hereby incorporated by reference in its entirety as if fully set forth herein.

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be constructed as restricted to the particularly described embodiments, and the scope and concept of the invention will be more readily understood by references to the claims, which follow.

The invention claimed is:

1. A process for the preparation of Efinaconazole of formula (1), comprising the steps of:
   a) reacting a compound of formula (2) with an organometallic alkylating agent capable of introducing an ethyl group, to form an alcohol of formula (3):

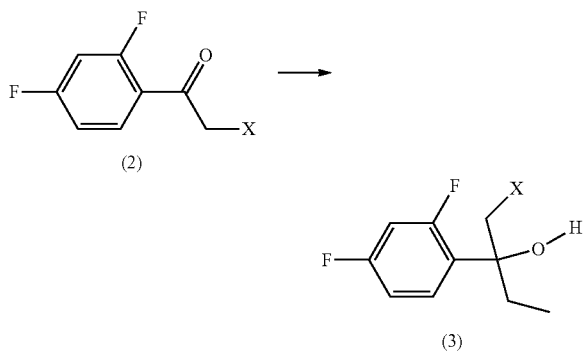

wherein X is a leaving group;

b) converting compound (3) to an alkene of formula (4):

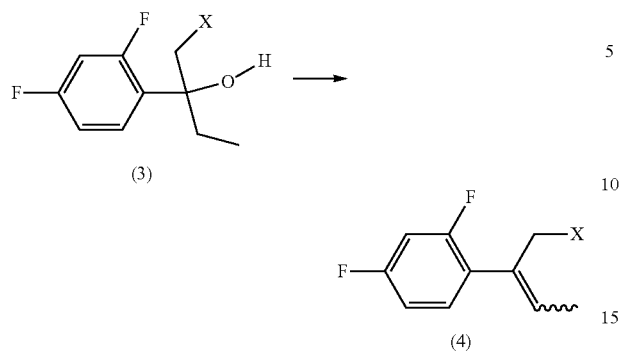

c) reacting alkene (4) with 1,2,4-triazole, to form 1-(2-(2,4-difluorophenyl)but-2-en-1-yl)-1H-1,2,4-triazole (5):

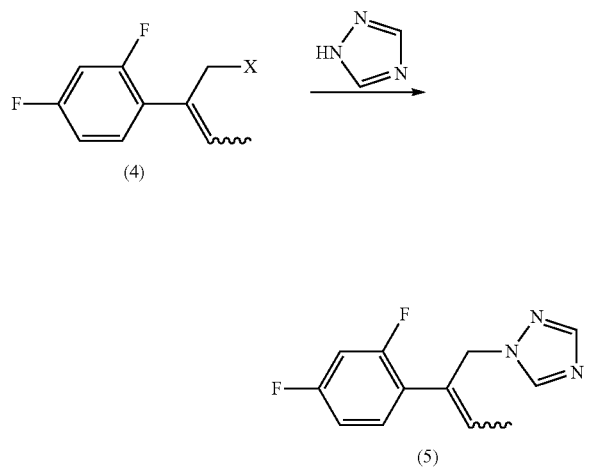

d) epoxidation of triazole-containing alkene (5), to form 1-((2-(2,4-difluorophenyl)-3-methyloxiran-2-yl)methyl)-1H-1,2,4-triazole (6);

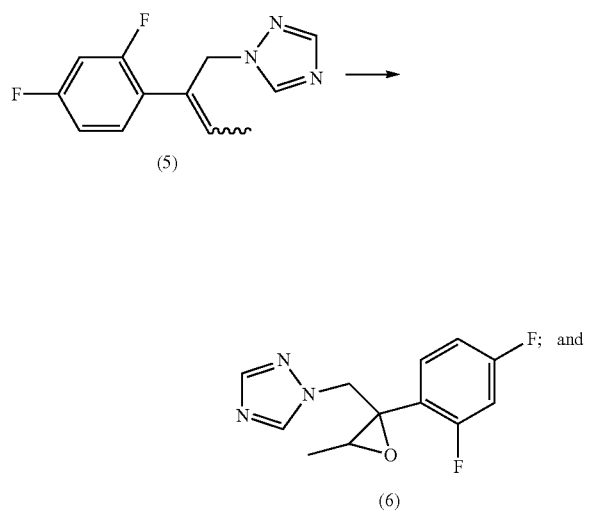

e) reacting epoxide (6) with 4-methylenepiperidine to form Efinaconazole of formula (1)

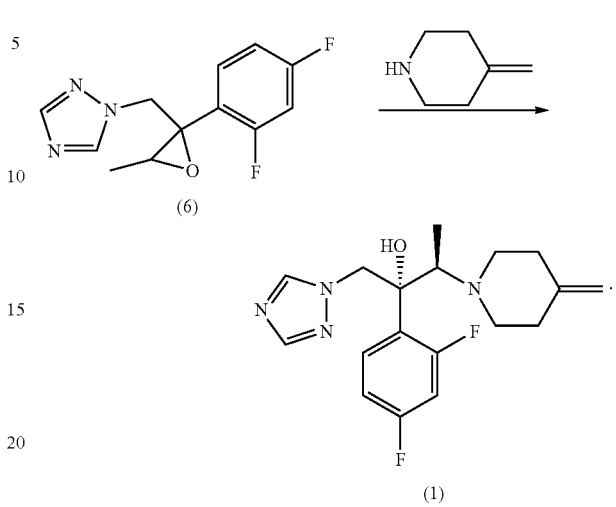

2. The process according to claim 1, wherein the leaving group is selected from the group consisting of halogen, sulfonyloxy and —OC(O)R' wherein R' is an alkyl, aryl or alkylaryl.

3. The process according to claim 2, wherein the leaving group is selected from the group consisting of Cl, Br, I, mesylate (OMs), triflate (OTr) and tosylate (OTs).

4. The process according to claim 1, wherein the organometallic alkylating agent is selected from ethyl lithium (EtLi) and ethyl magnesium halogenate (Et-Mg—Y wherein Y is halogen).

5. The process according to claim 4, wherein the organometallic alkylating agent is ethyl magnesium chloride or ethyl magnesium bromide.

6. The process according to claim 1, wherein step (b) is conducted in the presence of a dehydration agent.

7. The process according to claim 6, wherein the dehydration agent is a protic acid, preferably, sulfuric acid or phosphoric acid.

8. The process according to claim 1, wherein step (c) is conducted in the presence of a base.

9. The process according to claim 8, wherein the base is selected from the group consisting of metal hydrides, organometallic compounds, alcoholates, hydroxides, carbonates, bicarbonates, organic amines and basic resins.

10. The process according to claim 9, wherein the base is selected from metal hydrides and alcoholates, preferably wherein the metal hydride is selected from sodium hydride and potassium hydride, and the alcoholate is selected from NaOMe, NaOEt, t-BuONa and t-BuOK.

11. The process according to claim 8, wherein the reaction is conducted in a polar aprotic solvent selected from dimetylformamide (DMF), dimethylsulfoxide (DMSO) and N-methylpyrrolidone (NMP).

12. The process according to claim 1, wherein steps (a), (b) and (c) are conducted as "one-pot" synthesis without separation and purification of corresponding intermediates.

13. The process according to claim 1, wherein step (d) is carried out in the presence of an epoxidation agent, preferably, a peroxy organic acid.

14. The process according to claim 13, wherein the epoxidation agent is peroxymaleic acid.

15. The process according to claim 1, wherein X=Cl and the organometallic alkylating agent is ethyl magnesium halogenate (Et-Mg—Y), and the process comprises the steps of:

a) reacting a compound of formula (2') with ethyl magnesium halogenate to form 1-chloro-2-(2,4-difluorophenyl)butan-2-ol (3'):

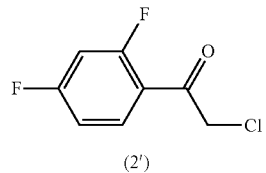

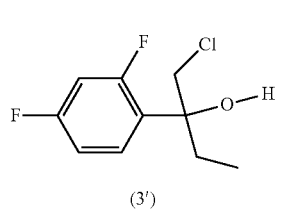

wherein Y is halogen;

b) converting alcohol (3') to an alkene of formula (4'):

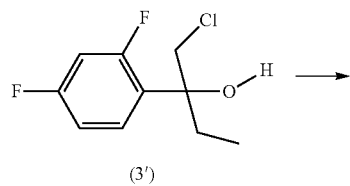

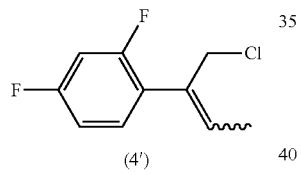

c) reacting alkene (4') with 1,2,4-triazole, to form 1-(2-(2,4-difluorophenyl)but-2-en-1-yl)-1H-1,2,4-triazole (5):

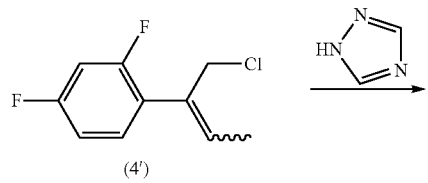 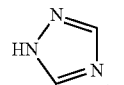

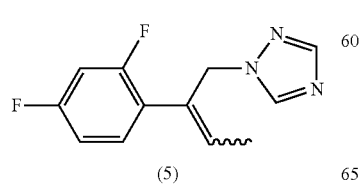

d) epoxidation of triazole-containing alkene (5), to form 1-((2-(2,4-difluorophenyl)-3-methyloxiran-2-yl)methyl)-1H-1,2,4-triazole (6);

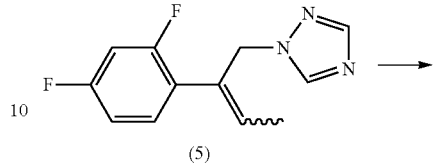

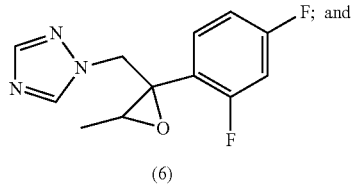

e) reacting epoxide (6) with 4-methylenepiperidine to form Efinaconazole of formula (1)

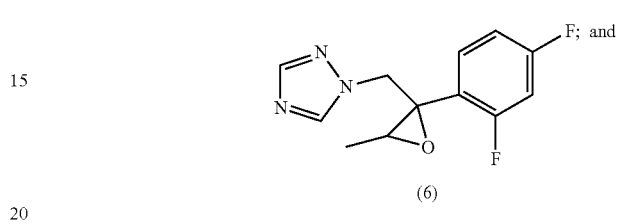

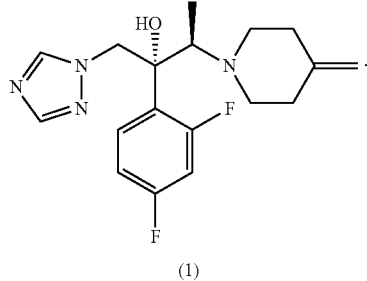

16. A compound represented by the structure of formula (3):

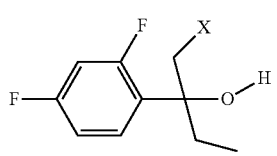

wherein X is a leaving group selected from the group consisting of Cl, Br, I, mesylate (OMs), triflate (OTr) and tosylate (OTs).

17. The compound according to claim 16, wherein X is Cl and the compound is represented by the structure of formula (3'):

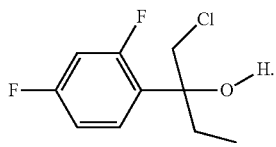
(3')

18. A compound represented by the structure of formula (4);

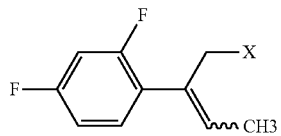
(4)

including (Z)- or (E)-isomers or mixtures thereof, wherein X is a leaving group selected from the group consisting of Cl, Br, I, mesylate (OMs), triflate (OTr) and tosylate (OTs).

19. The compound according to claim 18, wherein X is Cl and the compound is represented by the structure of formula (4'):

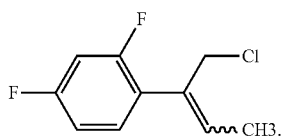
(4')

* * * * *